United States Patent [19]

Falkowski et al.

[11] 4,195,172
[45] Mar. 25, 1980

[54] SALTS OF N-GLYCOSYL DERIVATIVES OF POLYENE MACROLIDES, ESPECIALLY N-METHYLGLUCAMINE SALTS AS WELL AS THE METHOD OF THEIR PREPARATION

[75] Inventors: Leonard Falkowski, Gdańsk; Zuzanna Kowszyk-Gindifer; Zofia Płóciennik, both of Warsaw; Jan Zieliński, Gdańsk; Halina Dahlig, Warsaw; Jerzy Golik; Ewa Jakobs, both of Sopot; Pawel Kolodziejczyk; Elżbieta Bylec, both of Gdańsk; Danuta Roślik-Kamińska; Wladyslawa Wagner, both of Warsaw; Jan Pawlak, Sopot; Edward Borowski, Gdańsk, all of Poland

[73] Assignees: Politechnika Gdańska, Gdańsk; Instytut Przemyslu Farmaceutycznego, Warsaw, both of Poland

[21] Appl. No.: 905,178

[22] Filed: May 10, 1978

Related U.S. Application Data

[63] Continuation-in-part of Ser. No. 787,265, Apr. 13, 1977, abandoned.

[30] Foreign Application Priority Data

Apr. 22, 1976 [PL] Poland .................................. 188979

[51] Int. Cl.$^2$ .......................................... C07H 17/08
[52] U.S. Cl. ................................. 536/17 R; 424/180; 536/18; 536/22
[58] Field of Search ............................. 536/17, 18, 22

[56] References Cited

U.S. PATENT DOCUMENTS

| | | | |
|---|---|---|---|
| 2,383,977 | 9/1945 | Lee et al. | 536/22 |
| 2,760,865 | 8/1956 | Folkers | 536/19 |
| 4,007,166 | 2/1977 | Kulbakh et al. | 536/17 |
| 4,041,232 | 8/1977 | Sipos et al. | 536/4 |
| 4,093,796 | 6/1978 | Falkowski et al. | 536/17 |

Primary Examiner—Johnnie R. Brown
Attorney, Agent, or Firm—Haseltine, Lake & Waters

[57] ABSTRACT

The new compounds, N-methylglucamine salts of N-glycosyl derivatives of polyene macrolides particularly N-methylglucamine salts of N-glycosyl derivatives of amphotericin B, polifungin and nystatin are described herein. These compounds exhibit high pharamacological activity in some topical and sistemic fungal infections. The product is prepared by reaction of an amino group containing polyene macrolide with an aldose or ketose mono- or oligosaccharide, in an organic solvent medium or in the mixture of solvents characterized in that the formed N-glycosyl derivatives is precipitated from the reaction medium by water or with an aqueous solution of inorganic salt, preferably ammonium sulphate, and after crystallization from a higher alkanol of $C_{3-6}$ atoms, preferably n-butanol transformed into a salt, preferably an N-methylglucamine salt and then crystallized from higher alkanol, preferably n-butanol.

3 Claims, No Drawings

SALTS OF N-GLYCOSYL DERIVATIVES OF POLYENE MACROLIDES, ESPECIALLY N-METHYLGLUCAMINE SALTS AS WELL AS THE METHOD OF THEIR PREPARATION

This application is continuation-in-part of our co-pending application Ser. No. 787,265 filed Apr. 13, 1977, now abandoned.

The invention relates to the new N-methylglucamine salts of N-glycosyl derivatives of polyene macrolides, especially amphotericin B, polifungin, and nystatin of very high water solubility, as well as to the simplified method of their preparation.

The said compounds, similarly as polyene macrolides and their N-glycosyl derivatives, exhibit antifungal activity, especially against yeast-like fungi. There should be stressed their high activity against microorganisms of the genus Candida, Torula, Geotrichum as well as Cryptococcus.

From the literature and patents there have been known esters and salts of methyl esters of polyene macrolides, complex of amphotericin B and sodium deoxycholate i.e. Fungizone/Bartner E. et al: Studies on a new solubolized preparation of amphotericin B, Antib. Ann. 1957/1958, 53–58, 1958/, N-methylglucamine salts of polyene macrolides as well as sodium, tris and imidazole salts of N-glycosyl derivatives of polyene macrolides.

According to the U.S. Pat. No. 3,945,993 methyl esters of polyene macrolides are not soluble in water, and hydrochloride of methyl esters of amphotericin B, similarly as Fungizone, forms in water merely micelle/-Schaffner C. P., Mechliński W.; Polyene macrolide derivatives. II Physical-chemical properties of polyene macrolide esters and their water soluble salts, J. Antibiotics, 1972, 25, 259/.

From the U.S. Pat. No. 4,041,232 there have been known water soluble salts of methyl ester of amphotericin B with mono- and dicarboxylic amino acids, hydroxy carboxylic acids and mono- and dicarboxylic acids, water solubility of which is equal to 10%. The mentioned patent lacks however documented biological, pharmaco-kinetic data as well as information on stability of the said compounds.

Formation of the known from the U.S. Pat. No. 4,007,166 N-methylglucamine salt of polyene macrolides of a required solubility is conditioned by considerable, since fivefold excess of N-methylglucamine in relation to polyene macrolide. Therefore there are finally obtained solutions to the said salts in aqueous solution of N-methylglucamine base, and not in water.

Besides the above described derivatives of polyene macrolides there have been known from the British Pat. No. 1,397,187 water soluble sodium, tris and imidazole salts of N-glycosyl derivatives of polyene macrolides. However imidazole salts, as much more toxic, are not so advised for application in the form of injection, whereas application of sodium salts of N-glycosyl derivatives of polyene macrolides in the form of injection solutions is rendered difficult because of higher pH value in comparison with N-methylglucamine salts of N-glycosyl derivatives. Moreover the sodium salts of N-glycosyl derivatives of polyene macrolides in water solutions at such high pH value are labile, and the biological activity of appropriate pharmaceutical preparations in comparison with the activity of the parent substance being reduced. In IR spectrum the significant degradation of lactone ring was observed.

The present invention relates to production of the new, hitherto unknown and not described compounds from the group of polyene macrolides, especially N-methylglucamine salts of N-glycosyl derivatives of polyene macrolides. Compounds obtained by the method according to the invention, namely N-methylglucamine salts of N-glycosyl derivatives of polifungin and nystatin of the formula $C_{60}H_{102}O_{27}N_2$; M.W. = 1283.0 and amphotericin B of the formula $C_{60}H_{100}O_{27}N_2$, M.W. = 1281.0, have UV spectrum unchanged in comparison with original antibiotics as well as characterstic values of IR spectrum and specific absorption $/E_1\,cm^{1\%}/$ values.

Compounds, prepared by the method according to the invention, revealing high purity, activity and stability as well as containing advantageous from the pharmacological point of view, N-methylglucamine rest, as it appeared are very well soluble in water and also in water with the addition of glucose, and give fully clear solutions, what qualifies them for application as therapeutics, among others for parenteral administration, especially in the form of injections, what consisted the main aim of the carried out investigations. N-methylglucamine salts of N-glycosyl derivatives of polyene macrolides can be employed also in such forms as aerosols, infusions, vaginal tablets, moist applications as well as drops.

Method of preparing said compounds involves interaction of polyene macrolide antibiotic containing an amino group in organic solvent or mixture of solvents with mono- or oligosaccharide, i.e. aldose, ketose/-glucose, fructose, galactose or maltose/. The formed N-glycosyl derivatives of polyene macrolides precipitated from the reaction medium by water or aqueous solution of inorganic salt, preferably ammonium sulphate, which crystallize from the higher alkanol of $C_{3-6}$, preferably n-butanol, are transformed into salt, preferably N-methylglucamine salt, and crystallized from the higher alkanol, preferably n-butanol.

N-methylglucamine salts of N-glycosyl derivatives of polyene macrolides according to the invention consist the product of the reaction of nearly stoichiometric quantities of reagents in suitable conditions of the conducted process. The said method can be also used for production of another salts of N-glycosyl derivatives e.g. sodium and tris salt of N-glycosyl derivatives of antibiotics from the group of polyene macrolides.

The method of preparation of new, according to the invention, compounds is a continuous process, considerably simplified in comparison with the known prior art, warranting reproducibility with high yields at simultaneous achievement of exceptionally pure product not requiring additional purification. Elimination of diethyl ether and its replacement with water or aqueous solutions of inorganic salts secures safe carrying out the process of production. The product, in contradistinction to original antibiotics being labile, characterizes in high stability both in solid form as well as in the form of aqueous solutions and in the form of aqueous solutions of glucose, what at high and maintaining longer than in the case of Fungizone, level in the blood serum, consists one of elements exceptionally qualifying it for intravenous administration.

It should be stressed, that the method of carrying out the process in mild reaction conditions does not admit to inactivation of antibiotics, and products prepared by the method according to the invention, do not contain any contaminations, in it unreacted substances in contradistinction to methods known from the prior art, where isolation of derivatives and application of the purification method considerably protract the process and create the risk of inactivation of the antibiotic.

The N-methylglucamine salts are water soluble and show low pH value/table 1/, and their water solutions are stable/table 2/.

Table 1

| | Sodium salt of N-glycosyl derivative of polifungin | N-methyglucamine salt of N-glycosyl derivative of polifungin | Sodium salt of N-gylcosyl derivative of nystatin | N-methylglucamine salt of N-glycosyl derivative of nystatin |
|---|---|---|---|---|
| pH 1% water solution | 9.9 | 8.9 | 9.7 | 8.3 |
| Biological activity in U/mg | 1860 | 2365 | 1296 | 1780 |
| Solubility in water | 4–10% | >15% | 4–10% | >15% |

Exceptionally high water solubility of the said salts in comparison with the hitherto known derivatives of polyene macrolides, in it the only one applied as therapeutic form of amphotericin B/Fungizone/, giving water merely pseudosolutions, allows for their employment in the form of single intravenous injection instead of continuous intravenous drip, up-to-now being the only one form of application of Fungizone.

There has been tested also stability of water soluble N-methylglucamine salts of N-glycosyl derivatives of polyene macrolides and comparatively of Fungizone, being stored at different temperatures within 6 months/table 2/.

Table 2

| | Biological acitivity+/in % at temperatures: | | | |
|---|---|---|---|---|
| Antibiotic | +4° C. | RT | +37° C. | +50° C. |
| Fungizone | 89.1 | 92.7 | 88.8 | 51.3 |
| N-methylglucamine salt of N-glycosyl derivative of: | | | | |
| - amphotericin B | 81.2 | 83.1 | 77.0 | 79.8 |
| - polifungin | 92.3 | 100.4 | 100.9 | 100.4 |

+/initial biological activity was assumed as 100%

However, some of the new salts, for example the N-methylglucamine salt of N-glycosyl derivative of polifungin, on the contrary to the Fungizone exhibit activity against Trichomonas vaginalis. The said activity of the N-methylglucamine salt of the N-glycosyl derivative of polifungin against Trichomonas vaginalis is more than three times that of polifungin itself.

Additionally, these salts, for example N-methylglucamine salt of N-glucosyl derivative of amphotericin B, exhibit exhanced antifungal activity in comparison with that of the Fungizone against many microorganisms for instance, Torula sp., Geotrichum candidum and Cryptococcus neoformans. The in vitro activities of the N-methylglucamine salts of the N-glycosyl derivative of amphotericin B and Fungizone against some fungi are compared in Table 3.

Table 3

| | The minimal active concentration $CE_{10}$/in mcg/ml/ | |
|---|---|---|
| Fungi | N-methylglucamine salt of N-glycosyl derivative of amphotericin B | Fungizone |
| Torala sp. | 1.66 | 2.39 |
| Geotrichum candidum | 1.07 | 1.48 |
| Cryptococcus neoformans | 1.25 | 1.48 |

There is a different sensitivity of different strains, for example Candida sp. to the N-methylglucamine salt of the N-glycosyl derivative of amphotericin B and Fungizone. Statistically, the amount of to Fungizone insensitive strains is much higher than the amount of to N-methylglucamine salt of the said derivative insensitive strains. This especially concerns *Candida albicans* strains ZM, HM, and 1/75, *Candida tropicalis* strains JD and 20/75 and *Candida krusei* strains TS and 16/75, which are insensitive to Fungizone, but sensitive to N-methylglucamine salt of N-glycosyl derivative of amphotericin B.

The relative activity index representing the antibiotic activity in experimental chemotherapy of Candida albicans infected mice is much more advantageous for the N-methylglucamine salts of the N-glycosyl derivatives of polyene macrolides than for Fungizone/Table 4/.

Table 4

| Antibiotic | Relative activity index in *Candida albicans* mice infection |
|---|---|
| Fungizone | 1 |
| N-methylglucamine salt of N-glycosyl derivative of: | |
| - amphotericin B | 2.35 |
| - polifungin | 5.08 |
| - nystatin | 2.41 |

In intravenous administration to rats of N-methylglucamine salts of polyene macrolide N-glycosyl derivatives as compared to Fungizone the effect is much more advantageous for the N-methylglucamine salts because the presence of antibiotic in the serum after administration can be found longer that in the case of Fungizone/Table 5/.

Table 5

| Antibiotic | Time of the presence of an antibiotic in serum after 1/5 $DL_{50}$ dose administration /in minutes/ |
|---|---|
| Fungizone | 5 |
| N-methylglucamine salt of N-glycosyl derivative of: | |
| - amphotericin B | 15 |
| - polifungin | 60 |
| - nystatin | 30 |

The data representing the selective toxicity are also more advantageous for the N-methylglucamine salt of N-glycosyl derivatives of polyene macrolides than for Fungizone. The indices of selective toxicity $EK_{50}/DK_{50}$ and $EH_{50}/DK_{50}$, illustrating the ratio of the minimal antibiotic concentration causing 50% effluence of the potassium ions from erythrocytes of human blood/$EK_{50}$/and the minimal concentration of antibiotic causing 50% hemolysis of erythrocytes/$EH_{50}$/to the minimal antibiotic concentration causing 50% effluence of the potassium ions from *Saccharomyces cerevisiae* cells/$DK_{50}$/are compared in Table 6.

Table 6

| Antibiotic | Selective toxicity index | |
|---|---|---|
| | $\frac{EK_{50}}{DK_{50}}$ | $\frac{EH_{50}}{DK_{50}}$ |
| Fungizone | 1.09 | 1.4–2.9 |
| N-methylglucamine salt of N-glycosyl derivative of: | | |
| - amphotericin B | 1.37 | 24 |
| - polifungin | 11.4 | 31 |
| - nystatin | 17.3 | 45 |

On intravenous administration in mice the acute toxicity of N-methylglucamine salts of N-glycosyl derivatives of polyene macrolides is lower than that of Fungizone/Table 7/.

Table 7

| Antibiotic | $DL_{50}$ for mice in mg/kg body weight administered intravenously |
|---|---|
| Fungizone | 7.4–9.3 |
| N-methylglucamine salt of N-glycosyl derivative of: | |
| - amphotericin B | 12.1–14.3 |
| - polifungin | 13.8–16.4 |
| - nystatin | 19 |

The N-methylglucamine salts of the N-glycosyl derivatives of polyene macrolides may be used in the treatment of topical and systemic fungal infections, caused by fungi: *Candida albicans, Cryptococcus neoformans,* Aspergillus, Geotrichum, Torulopsis and others.

In a case of generalized *geotrichosis* caused by *Geotrichum candidum* and *aspergillosis* caused by *Aspergillus fumigatus*, N-methylglucamine salts of N-glycosyl polifungin and N-glycosyl nystatin reveal in vivo higher activity than Fungizone. In these cases activity of N-methylglucamine salt of N-glycosyl amphotericin B corresponds to activity of Fungizone/Table 8/.

Table 8

| Antibiotic | Average protective $DP_{50}$ doses for mice in mg/kg/ 24 hours in a case of generalized | |
|---|---|---|
| | geotrichosis | aspergillosis |
| Fungizone | 20.6 | 26.4 |
| N-methylglucamine salt of N-glycosyl derivative of: | | |
| - amphotericin B | 17.9 | 22.7 |
| - polifungin | 3.81 | 4.54 |
| - nystatin | 4.49 | 6.28 |

EXAMPLE I 1 g of amphotericin B and 0.3 g of glucose suspended in 15 ml of dimethyl formamide and were allowed to stand at a temperature of 37° C. for 20 hours. The N-glycosyl derivative was precipitated with 300 ml of 5% ammonium sulphate, aqueous solution, and washed with 50 ml of water. The precipitate was suspended in 50 ml of methanol and 40 ml of n-butanol, whereupon 0.1 mM of sodium carbonate in 10 ml of water was added. Methanol and water as an azeotropic mixture with n-butanol were evaporated and the residue was allowed to crystallize. 1.2 g of sodium salt of the N-glycosyl derivative of the amphotericin B of $E_{1\ cm}^{1\%}=1200$ at 380 and $IC_{50}=0.05$ mcg/ml were obtained.

EXAMPLE II 1 g of amphotericin B and 0.3 g of glucose was suspended in 15 ml of dimethyl formamide and allowed to stand for 20 hours at a temperature of 37° C. The N-glycosyl derivative was precipitated with 300 ml of 5% ammonium sulphate aqueous solution. The precipitate was washed with 50 ml of water, dissolved in 50 ml of methanol and 1 mM of tris and 40 ml of n-butanol was added, then methanol and water as azeotropic mixture with n-butanol was distilled and the residue was left for crystallization. The tris salt of the N-glycosyl derivative of amphotericin B of $E_{1\ cm}^{1\%}=1040$ at 380 nm and $IC_{50}=0.6$ mcg/ml was obtained.

EXAMPLE III 3 g of polifungin was suspended in 15 ml of dimethyl formamide, 0.9 g of glucose was added and allowed to stand at a temperature of 38° C. for 24 hours. The insoluble residue was centrifuged and N-glycosyl derivative was precipitated from the filtrate with 1 l of 5% ammonium sulphate aqueous solution. The precipitate was centrifuged and extracted three times with 40 ml of methanol at a temperature of 38° C. 3 mM tris was added to the solution, then 40 ml of n-butanol, whereupon methanol and water as azeotropic mixture with n-butanol was evaporated and the residue was left for crystallization at a temperature of $-5°$ C. 2.85 g of the tris salt of N-glycosyl derivative of polifungin of $E_{1\ cm}^{1\%}=570$ at 304 nm and $IC_{50}=0.4$ mcg/ml were obtained. Original antibiotic: $E_{1\ cm}^{1\%}=660$ at 304 nm, $IC_{50}=0.15$ mcg/ml.

EXAMPLE IV 20 g of polifungin and 6 g of glucose were dissolved in 100 ml of dimethyl formamide and allowed to stand at a temperature of 36° C. for 18 hours. The resulting solution was filtered, then 400 ml of 5% ammonium sulphate, aqueous solution, was added to the filtrate and allowed to stand at a temperature of $+4°$ C. for 2 hours. The precipitate was filtered and washed with water and then extracted three times using 800 ml of methanol for each portion. 6 g of N-methylglucamine was dissolved in 60 ml of water and added to the methanol extracts. 1000 ml of n-butanol was added to this solution whereupon the reaction mixture was evaporated at a temperature of 45° C. under reduced pressure to remove methanol and water. The residue was allowed to stand at a temperature of $+4°$ C. for crystallization. The precipitate was filtered and washed with n-butanol, then with petroleum ether and was dried at a room temperature. 16.5 g of the N-methylglucamine salt of the N-glycosyl derivative of polifungin of $E_{1\ cm}^{1\%}=560$ at 304 nm and $IC_{50}=0.42$ mcg/ml was obtained. Original antibiotic: $E_{1\ cm}^{1\%}=660$ at 304 nm and $IC_{50}=0.16$ mcg/ml.

EXAMPLE V 20 g of polifungin and 6 g of glucose were dissolved in 100 ml of dimethyl formamide and then the further procedure was carried out as in the Example IV till the moment of washing with water of precipitated N-glycosyl polifungin. The washed precipitate was suspended in 1200 ml of methanol of the temperature of 50° C., then was stirred and 7 g of N-methylglucamine, dissolved in 70 ml of water, were added. After dissolving the solution was filtered, 800 ml of n-amyl alcohol were added and the whole was concentrated under the reduced pressure at the temperature of 40° C. till the moment of removal of methanol and water. The resulting precipitate was filtered and washed with acetone. The precipitate was dried at a room temperature under the reduced pressure. 16.3 g of N-methylglucamine salt of N-glycosyl polifungin of biological activity of 1980 U/mg, $E_1 \, _{cm}^{1\%} = 572$ at 304 nm were obtained. Original antibiotic exhibited $E_1 \, _{cm}^{1\%} = 720$ at 304 nm.

EXAMPLE VI 20 g of polifungin and 6 g of glucose were dissolved in 100 ml of dimethyl formamide and then the procedure was carried out as in the Example V, but instead of n-amyl alcohol there was used n-propyl alcohol in the same quantity as n-amyl one. 16.0 g of N-methylglucamine salt of N-glycosyl polifungin, soluble in water, of biological activity of 2010 U/mg, $E_1 \, _{cm}^{1\%} = 558$ at 304 nm were obtained. Original antibiotic: $E_1 \, _{cm}^{1\%} = 720$ at 304 nm.

EXAMPLE VII 20 g of nystatin and 6 g of glucose was dissolved in 100 ml of dimethyl formamide. Further procedure was carried out as given in Example IV 18 g of the N-methylglucamine salt of the N-glycosyl derivative of nystatin of $E_1 \, _{cm}^{1\%} = 560$ at 304 nm and $IC_{50} = 0.45$ mcg/ml was obtained. Original antibiotic: $E_1 \, _{cm}^{1\%} = 790$ at 304 nm, $IC_{50} = 0.18$ mcg/ml.

EXAMPLE VIII 20 g of amphotericin B and 6 g of glucose was dissolved in 200 ml of dimethyl formamide and allowed to stand at a temperature of 35° C. for 18 hours. The resulting solution was filtered and 500 ml of 5% ammonium sulphate, aqueous solution, was added to the filtrate the mixture was then allowed to stand at a temperature of +40° C. for 2 hours. The precipitate was filtered and washed with water. 1500 ml of methanol at a temperature of 50° C. and 6 g of N-methylglucamine salt dissolved in 60 ml of water was added to the precipitate whereupon the mixture was stirred for 30 minutes, then 1 l of n-butanol was added. The resulting solution was evaporated at a temperature of 45° C. under reduced pressure until the methanol and water were removed. The residue was allowed to stand at a temperature of +4° C. for crystallization. The sediment was filtered, washed with n-butanol then with petroleum ether and dried at the room temperature. 18 g of the N-methylglucamine salt of N-glycosyl derivative of amphotericin B of $E_1 \, _{cm}^{1\%} = 1140$ at 380 nm and $IC_{50} = 0.1$ mcg/ml were obtained.

EXAMPLE IX 5 g of polifungin and 1.5 g of fructose were suspended in 50 ml of dimethyl formamide and next the procedure was carried out as in the Example IV. 4.4 g of N-methylglucamine salt of N-glycosyl polifungin of $E_1 \, _{cm}^{1\%} = 562$ at 304 nm and $IC_{50} = 0.46$ mcg/ml were obtained. Original antibiotic: $E_1 \, _{cm}^{1\%} = 660$ at 304 nm and $IC_{50} = 0.16$ mcg/ml.

EXAMPLE X 5 g of nystatin and 1.5 g of galactose were suspended in 50 ml of dimethyl formamide and next the procedure was carried out as in Example IV. 4.2 g of N-methylglucamine salt of N-glycosyl nystatin of $E_1 \, _{cm}^{1\%} = 600$ at 304 nm and $IC_{50} = 0.45$ mcg/ml were obtained. Original antibiotic: $E_1 \, _{cm}^{1\%} = 790$ at 304 nm, $IC_{50} = 0.18$ mcg/ml.

EXAMPLE XI 5 g of nystatin and 3.0 g of maltose were suspended in 50 ml of dimethyl formamide and next the procedure was carried out as in Example IV. 4.5 g of N-methylglucamine salt of N-glycosyl nystatin of $E_1 \, _{cm}^{1\%} = 580$ at 304 nm and $IC_{50} = 0.45$ mcg/ml were obtained. Original antibiotic exhibited: $E_1 \, _{cm}^{1\%} = 790$ at 304 nm and $IC_{50} = 0.18$ mcg/ml.

What we claim is:

1. N-methylglucamine salt of the N-glycosyl derivative of amphotericin B.
2. N-methylglucamine salt of the N-glycosyl derivative of polifungin.
3. N-methylglucamine salt of the N-glycosyl derivative of nystatin.

* * * * *